United States Patent
Wu et al.

(10) Patent No.: US 8,048,132 B2
(45) Date of Patent: Nov. 1, 2011

(54) SPINE FIXATION DEVICE

(75) Inventors: Ming-Chang Wu, Guishan Shiang (TW); Jia-Jyun Hong, Guishan Shiang (TW); Chi-Bin Wu, Guishan Shiang (TW)

(73) Assignee: AccuMIS Inc., Zhonghe, Taipei (TW)

( * ) Notice: Subject to any disclaimer, the term of this patent is extended or adjusted under 35 U.S.C. 154(b) by 328 days.

(21) Appl. No.: 12/535,918

(22) Filed: Aug. 5, 2009

(65) Prior Publication Data
US 2011/0004245 A1    Jan. 6, 2011

(30) Foreign Application Priority Data
Jul. 3, 2009 (TW) .............................. 98122632 A

(51) Int. Cl.
*A61B 17/86* (2006.01)
(52) U.S. Cl. ........ 606/305; 606/306; 606/308; 606/301; 606/264; 606/278
(58) Field of Classification Search .......... 606/300–321, 606/264–276; 411/396–403, 340, 349; *A61B 17/58, A61B 17/86*
See application file for complete search history.

(56) References Cited

U.S. PATENT DOCUMENTS

| | | | |
|---|---|---|---|
| 5,658,285 A * | 8/1997 | Marnay et al. ................. 606/264 |
| 6,077,262 A * | 6/2000 | Schlapfer et al. .............. 606/305 |
| 6,485,491 B1 * | 11/2002 | Farris et al. .................... 606/250 |
| 6,736,820 B2 * | 5/2004 | Biedermann et al. ......... 606/308 |
| 2001/0001119 A1 * | 5/2001 | Lombardo ....................... 606/73 |
| 2005/0033296 A1 * | 2/2005 | Bono et al. ...................... 606/61 |
| 2005/0177154 A1 * | 8/2005 | Moumene et al. .............. 606/61 |
| 2006/0004357 A1 * | 1/2006 | Lee et al. ........................ 606/61 |
| 2008/0086131 A1 * | 4/2008 | Daly et al. ...................... 606/61 |
| 2009/0036934 A1 * | 2/2009 | Biedermann et al. ......... 606/301 |
| 2009/0082814 A1 * | 3/2009 | Bickley et al. ................. 606/286 |
| 2009/0143827 A1 * | 6/2009 | Levy et al. ..................... 606/308 |
| 2010/0262195 A1 * | 10/2010 | Jackson ......................... 606/305 |
| 2010/0331889 A1 * | 12/2010 | Abdou ........................... 606/264 |

FOREIGN PATENT DOCUMENTS
TW         M318410       9/2007

* cited by examiner

*Primary Examiner* — Thomas C. Barrett
*Assistant Examiner* — Jacqueline Johanas
(74) *Attorney, Agent, or Firm* — Stites & Harbison PLLC; Juan Carlos A. Marquez, Esq.

(57) ABSTRACT

A spine fixation device is provided. The spine fixation device includes a bone screw, a fixation carrier, and a first locking member. The fixation carrier is rotatably coupled to a fixation unit of the bone screw. The first locking member conjugates the fixation carrier and the bone screw together. A screw unit of the bone screw is implanted into a vertebra. As the fixation carrier is rotatably coupled to the bone screw, the bone screw remains fastened to the vertebra while the fixation carrier is rotated. Through rotational adjustment of the fixation carrier, U-shaped openings of the fixation carrier are adjustable in direction. Thus, the disposition angle of a rod disposed in the U-shaped openings is easily adjustable by rotating the fixation carrier. As a result, the rod can fit an angle of the spine while surgical complexity is reduced.

13 Claims, 6 Drawing Sheets

SPINE FIXATION DEVICE

BACKGROUND OF THE INVENTION

1. Technical Field

The present invention relates to a spine fixation device and, more particularly, to a spine fixation device for vertebral fixation.

2. Description of Related Art

A human spine should resemble a straight line when viewed from the front or back. Scoliosis refers to lateral curvature of the spine and may be inherited or result from a long-term improper body posture or trauma, among other possible causes. A person with scoliosis may have his or her body curved from side to side. In addition to an unsightly body shape, scoliosis tends to cause soreness and pain in the back. If left untreated, scoliosis may lead to degenerative arthritis as a result of uneven exertion of force for a long time. Moreover, an excessively large lateral vertebral curvature may even impair cardiopulmonary functions.

Patients with excessively large lateral vertebral curvatures are often treated by implanting spine fixation devices into the vertebrae from the sides. The spine fixation devices, composed essentially of bone screws and rods, not only prevent the patients' vertebral lateral curvatures from increasing, but also have corrective functions so as to ameliorate the symptoms of scoliosis.

However, a conventional spine fixation device has a large volume and therefore ends up with a large postoperative wound. Furthermore, during implantation of the conventional spine fixation devices, a surgeon must spend a lot of time to ensure that the bone screws and the rods are accurately located and that all the rods are precisely interconnected. In consequence, the operation time is undesirably long.

Taiwan Patent Publication No. M318410 discloses a pivotal connection structure for a fixation frame of a spinal correction device, wherein the fixation frame comprises a fixation carrier, a fixation assembly, and a pivotal connection element. The fixation carrier is formed with an installation hole for receiving the pivotal connection element. The fixation carrier is coupled to an end of a bone screw by means of the pivotal connection element. A rod is fixedly provided in the fixation carrier via the fixation assembly.

According to the disclosure of the above-cited Taiwan Patent Publication, the installation of the pivotal connection element in the fixation carrier allows the fixation carrier to be coupled rapidly to the bone screw, thereby facilitating subsequent installation of the rod, as well as enhancing the efficiency of spinal surgery. When two adjacent rods are not aligned with each other, angular adjustment of the rods is required. However, adjustment of the rods is impossible if the fixation frames are already coupled to the corresponding bone screws. In such a case, complexity of the spinal surgery will be increased. Besides, the problem of large postoperative wounds remains unsolved.

BRIEF SUMMARY OF THE INVENTION

The present invention provides a spine fixation device, wherein a fixation carrier is rotatable, such that U-shaped openings of the fixation carrier can be angularly adjusted as needed. Hence, a rod disposed in the U-shaped openings is also angularly adjustable, thereby reducing surgical complexity.

The present invention provides a spine fixation device, wherein a rod is angularly adjustable by a fixation carrier. Therefore, the spine fixation device only need to be implanted where abnormal vertebral curvature takes place, thereby minimizing postoperative wounds, accelerating recovery, and facilitating postoperative care.

To achieve the above and other effects, the present invention provides a spine fixation device including a bone screw, a fixation carrier, and a first locking member. The bone screw includes a screw unit and a fixation unit formed at a top end of the screw unit. The fixation unit has a top surface provided with an annular groove, wherein the annular groove has a center defined by a center of the top surface. The top surface of the fixation unit is centrally provided with a threaded hole. In addition, the top surface of the fixation unit has an edge extending upward so as to form a first stop plate. The fixation carrier includes a hollow body, a first extension unit, and a second extension unit. The hollow body has a wall formed with a pair of corresponding U-shaped openings. The first extension unit extends downward from the hollow body and has a lateral portion extending outward to form a second stop plate. The second stop plate is rotatable between a first end and a second end of the first stop plate. Moreover, the first extension unit is formed with an aperture corresponding in position to the threaded hole such that the aperture is in communication with the hollow body. The second extension unit extends downward from the first extension unit so as to form a hollow annular projection to be rotatably coupled to the annular groove. The first locking member can be locked in the threaded hole through the aperture, thereby conjugating the bone screw with the fixation carrier.

Implementation of the present invention at least involves the following inventive steps:

1. As the fixation carrier is rotatable, the rod disposed in the fixation carrier is angularly adjustable, thereby reducing surgical complexity.

2. With the rod being angularly adjustable, it is possible to make small-range spinal correction only where abnormal vertebral curvature takes place, thereby achieving the effect of minimally invasive surgery.

BRIEF DESCRIPTION OF THE SEVERAL VIEWS OF THE DRAWINGS

The invention as well as a preferred mode of use, further objectives, and advantages thereof will be best understood by referring to the following detailed description of illustrative embodiments in conjunction with the accompanying drawings, wherein.

DETAILED DESCRIPTION OF THE INVENTION

Figure 1A:
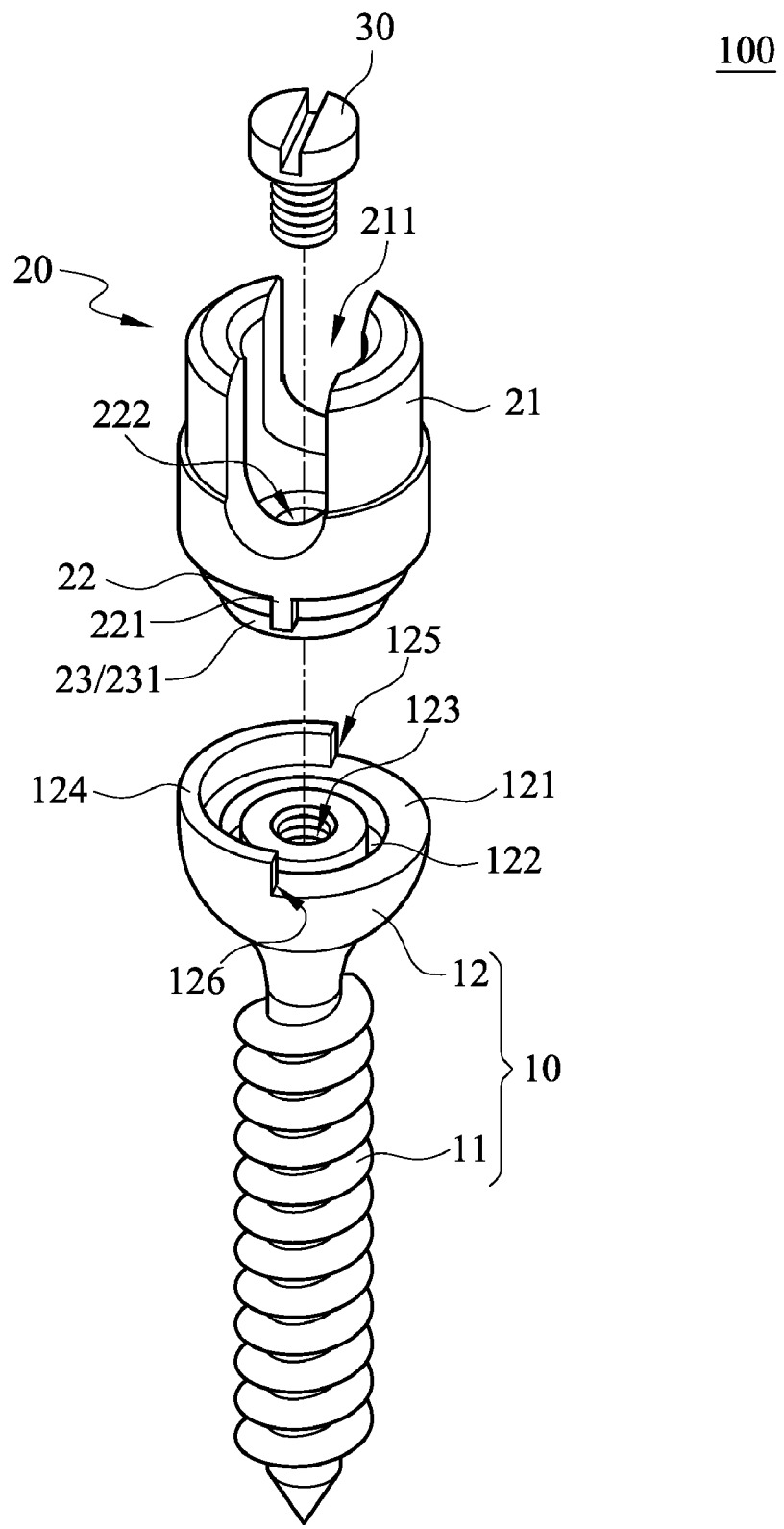
FIG. 1A is an exploded perspective view of a spine fixation device according to an embodiment of the present invention.

Referring to FIG. 1A, a spine fixation device 100 according to an embodiment of the present invention includes a bone screw 10, a fixation carrier 20, and a first locking member 30.

As shown in FIG. 1A, the bone screw 10 includes a screw unit 11 and a fixation unit 12. The bone screw 10 is made of a metal or a metal alloy. The screw unit 11 is configured for being implanted into a vertebra, thereby securing the spine fixation device 100 in position in the vertebra. The fixation unit 12 is formed at a top end of the screw unit 11. Moreover, the fixation unit 12 and the screw unit 11 can be integrally formed.

The fixation unit 12 has a top surface 121, which is a surface of the fixation unit 12 that faces away from the screw unit 11. The top surface 121 is provided with an annular groove 122, wherein a center of the top surface 121 defines a center of the annular groove 122. In addition, the top surface 121 is centrally formed with a threaded hole 123. The top surface 121 also has an edge extending upward so as to form a first stop plate 124. The first stop plate 124 is formed along the edge of the top surface 121.

As shown in FIG. 1A, the first stop plate 124 is an arcuate stop plate formed only along a part of the edge of the top surface 121. The first stop plate 124 has two corresponding ends, namely a first end 125 and a second end 126.

Figure 1B:
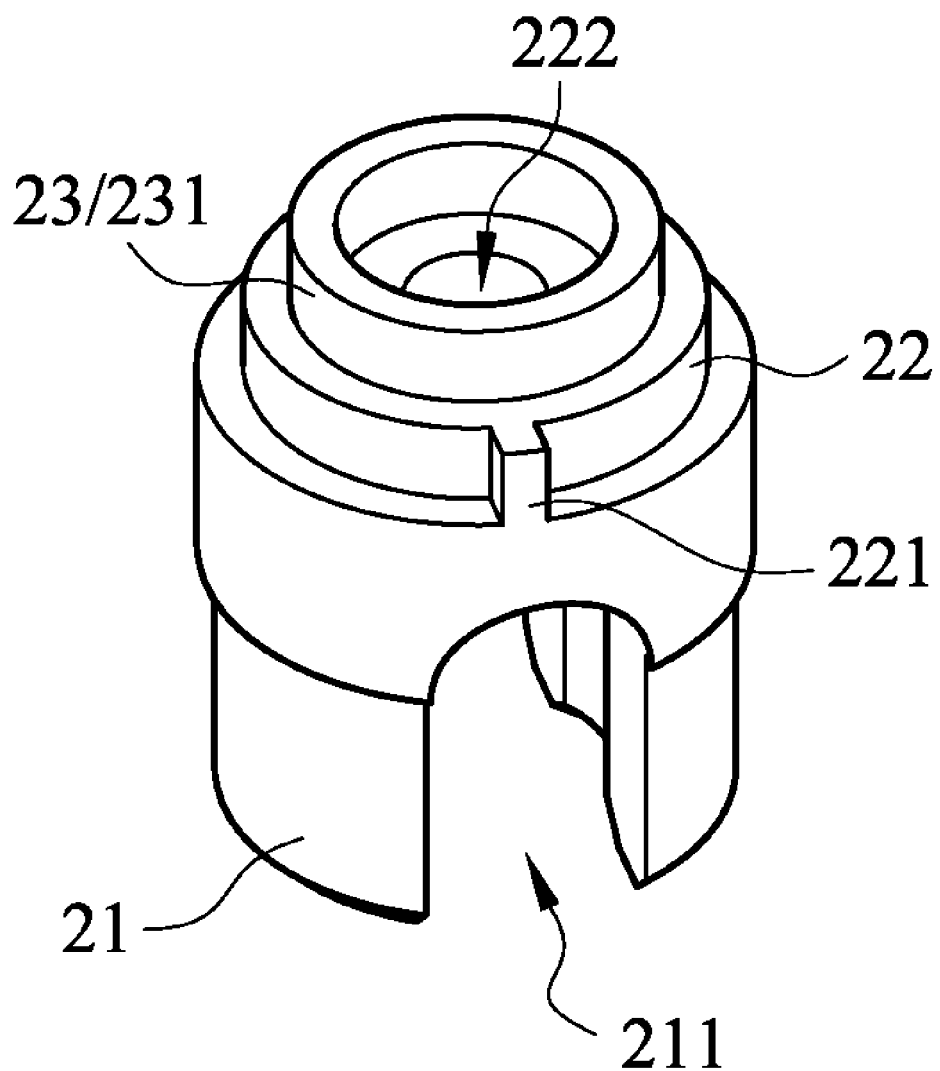
FIG. 1B is a perspective bottom view of a fixation carrier according to the present invention.

With reference to FIG. 1A and FIG. 1B, the fixation carrier 20 includes a hollow body 21, a first extension unit 22, and a second extension unit 23. The fixation carrier 20 is made of a metal or a metal alloy.

As shown in FIG. 1A and FIG. 1B, the hollow body 21 is a hollow cylinder. The hollow body 21 has a wall formed with a pair of corresponding U-shaped openings 211. The first extension unit 22 of the fixation carrier 20 extends downward from the hollow body 21. Besides, the first extension unit 22 has a lateral portion extending outward to form a second stop plate 221. Therefore, when the fixation carrier 20 and the fixation unit 12 are conjugated together, as shown in FIG. 2, the second stop plate 221 is rotatable between the first end 125 and the second end 126 of the first stop plate 124, i.e., rotatable along the edge of the top surface 121 of the fixation unit 12.

Figure 2:
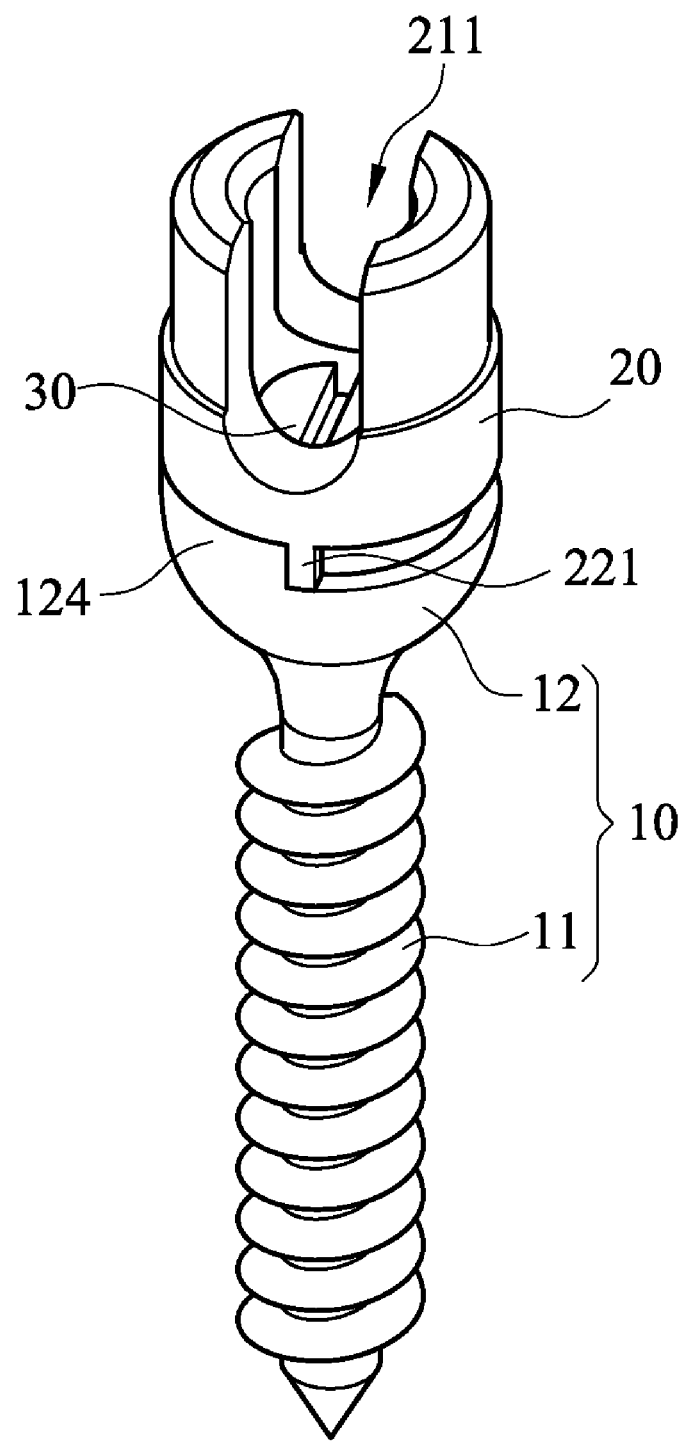
FIG. 2 is an assembled perspective view of the spine fixation device depicted in FIG. 1A.

Referring to FIG. 1A, FIG. 1B, and FIG. 2, the first extension unit 22 of the fixation carrier 20 is formed with an aperture 222 corresponding in position to the threaded hole 123 of the fixation unit 12. The aperture 222 is in communication with a hollow portion of the hollow body 21 such that, after the fixation carrier 20 and the fixation unit 12 are conjugated together, the hollow portion of the fixation carrier 20 is in communication with the threaded hole 123.

The second extension unit 23 of the fixation carrier 20 extends downward from the first extension unit 22 so as to form a hollow annular projection 231. The hollow annular projection 231 can be rotatably coupled to the annular groove 122 of the fixation unit 12, thus allowing the hollow annular projection 231 to rotate in the annular groove 122. In other words, it is possible to rotate only the hollow annular projection 231 of the fixation carrier 20, and while the hollow annular projection 231 is rotated, the annular groove 122 of the fixation unit 12 will not be rotated along with the hollow annular projection 231. Hence, rotation of the hollow annular projection 231 will not drive the screw unit 11 of the bone screw 10 to rotate, and in consequence the screw unit 11 remains securely locked in the vertebra.

As shown in FIG. 1A and FIG. 2, after the fixation unit 12 and the fixation carrier 20 are conjugated together, the rotation angle of the fixation carrier 20 is restricted by the first stop plate 124. More specifically, the second stop plate 221 is restricted by the first stop plate 124 and is rotatable only between the first end 125 and the second end 126 of the first stop plate 124. Therefore, if the first stop plate 124 is formed along a portion of the edge of the top surface 121, the second stop plate 221 is rotatable only along the remaining portion of the edge of the top surface 121. For instance, if the first stop plate 124 is formed along half of the edge of the top surface 121, the fixation carrier 20 has a rotation angle of 180 degrees. By rotating the fixation carrier 20, the U-shaped openings 211 of the fixation carrier 20 can be adjusted in direction. Preferably, the screw unit 11 will not get loose during rotational adjustment of the fixation carrier 20.

As shown in FIG. 1A, FIG. 1B, and FIG. 2, the first locking member 30 is locked in the threaded hole 123 of the fixation unit 12 through the aperture 222 of the fixation carrier 20, thereby conjugating the bone screw 10 with the fixation carrier 20 tightly. The first locking member 30 is made of a metal or a metal alloy.

Figure 3:
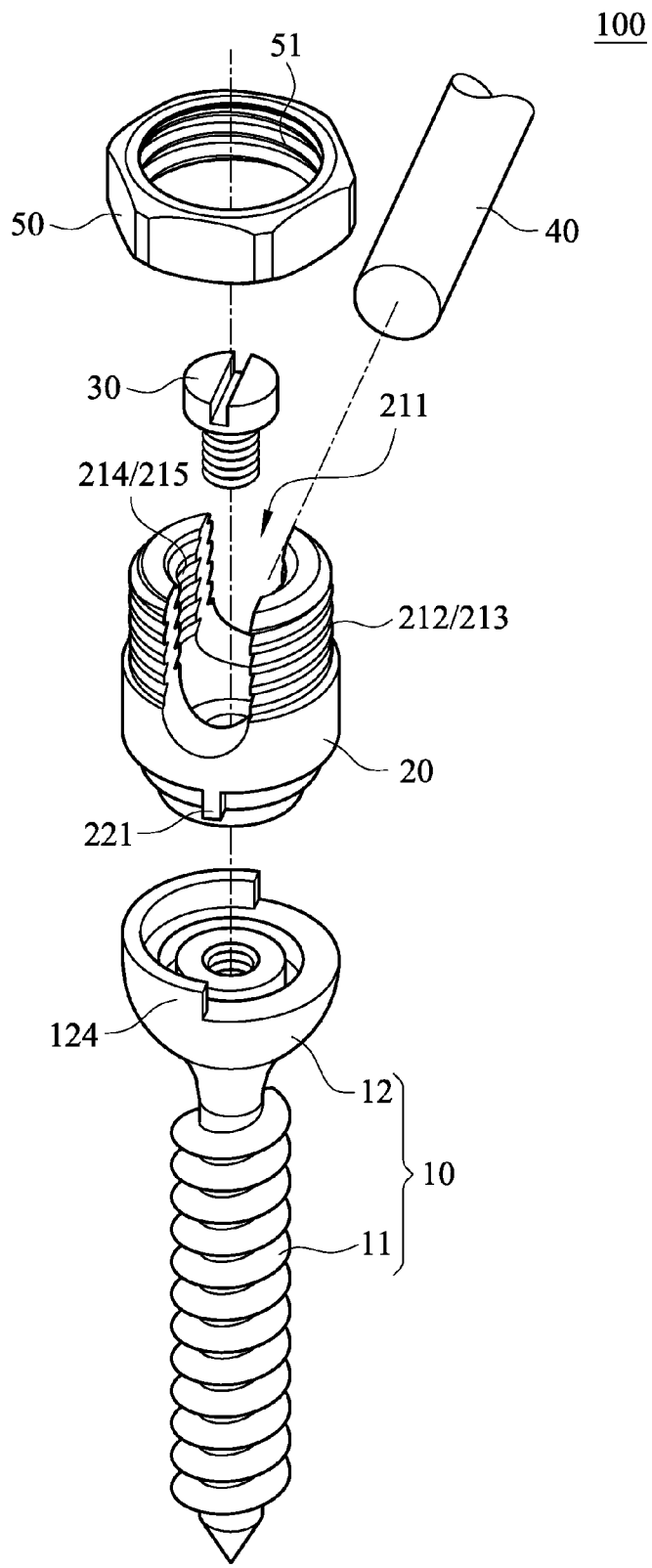
FIG. 3 is an exploded perspective view of a spine fixation device according to another embodiment of the present invention.

Referring to FIG. 3, the spine fixation device 100 further includes a rod 40 made of a metal or a metal alloy. The rod 40 is disposed in the U-shaped openings 211 of the fixation carrier 20 so as to be supported by the U-shaped openings 211. Hence, the disposition angle of the rod 40, i.e., the angle between the rod 40 and the spine, is adjustable by rotating the fixation carrier 20.

In addition, the hollow body 21 has an outer surface 212 provided with a first thread structure 213. Meanwhile, the spine fixation device 100 further includes a second locking member 50 made of a metal or a metal alloy. The second locking member 50 is internally provided with a second thread structure 51 engageable with the first thread structure 213. Thus, the rod 40 can be fixed in position to the fixation carrier 20 by means of the second locking member 50.

Figure 4:
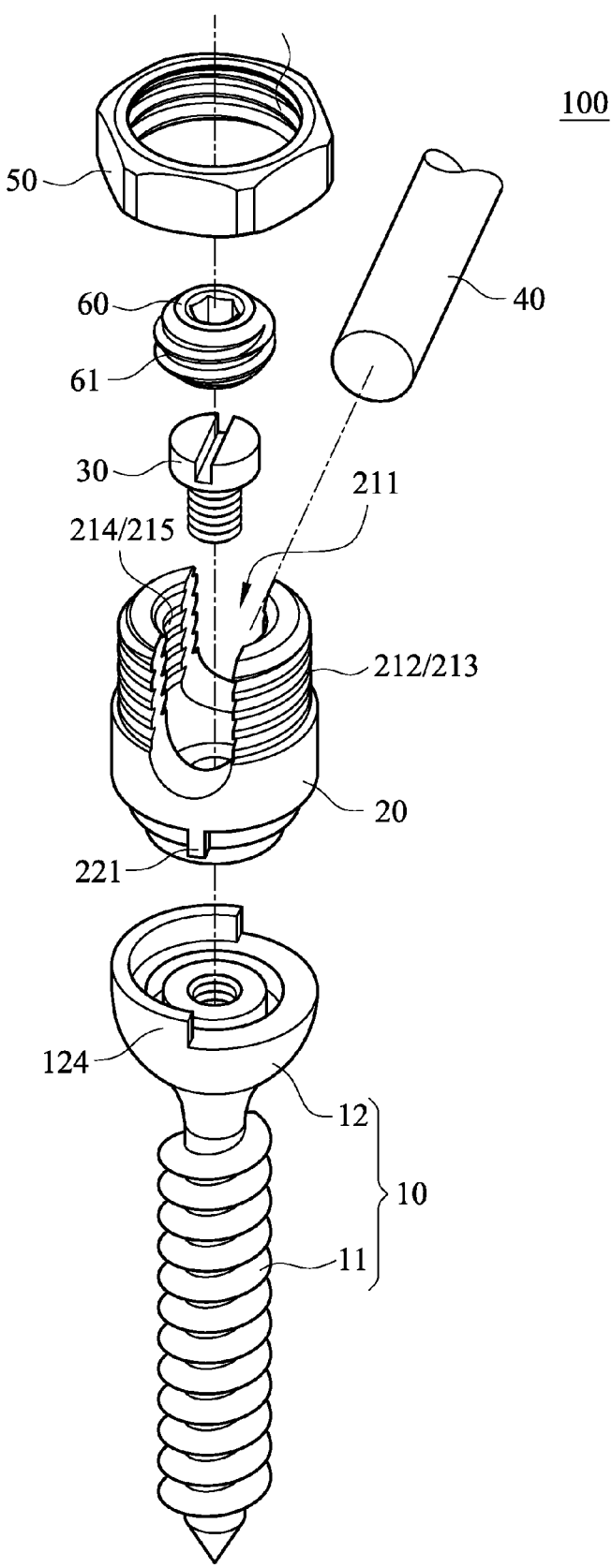
FIG. 4 is an exploded perspective view of a spine fixation device according to yet another embodiment of the present invention.

Referring to FIG. 4, the hollow body 21 further has an inner surface 214 provided with a third thread structure 215. At the same time, the spine fixation device 100 further includes a third locking member 60 made of a metal or a metal alloy. The third locking member 60 is externally provided with a fourth thread structure 61 engageable with the third thread structure 215. Therefore, via the third locking member 60, the rod 40 is fixed in position to the fixation carrier 20 with increased secureness.

Figure 5:
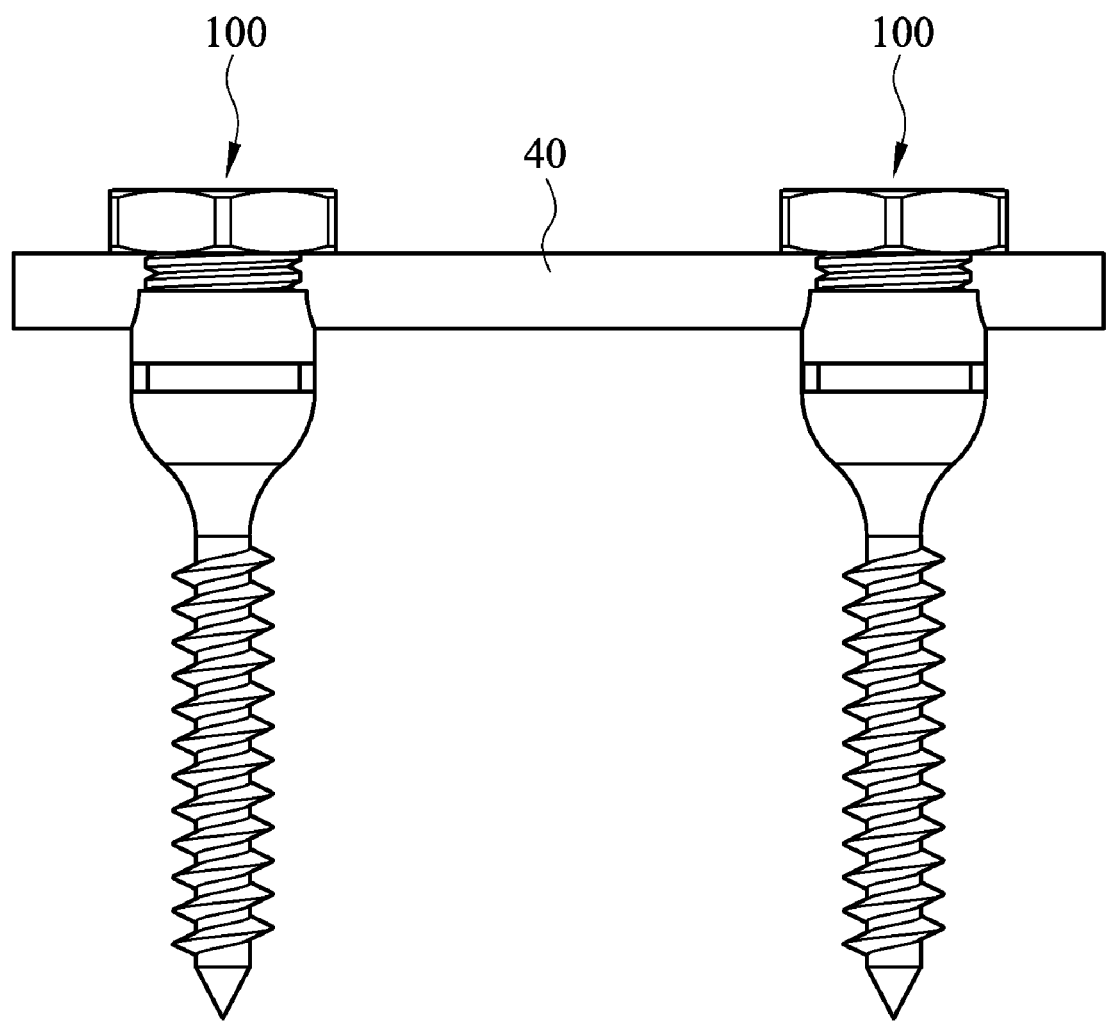
FIG. 5 is a side elevation view showing application of the spine fixation device according to the present invention.

Referring to FIG. 5, the rod 40 is installed between a pair of the above-described spine fixation devices 100. The design of the fixation carrier 20 and the fixation unit 12 allows the U-shaped openings 211 to be rotated and thereby adjusted in direction. Hence, the disposition angle of the rod 40 is adjustable. When it is required to use a plurality of rods 40 in a scoliosis corrective surgery, the rotational adjustment function of the present invention enables precise interconnection between the rods 40, which helps fix the spine in the accurate position. In doing so, surgical complexity is also reduced.

Besides, with the disposition angle of the rod 40 being adjustable, it is feasible to implant the spine fixation devices 100 only into vertebrae that need correction, thus minimizing the extent of surgery and the wound area. In other words, with the present invention, the effect of minimally invasive surgery can be achieved.

The foregoing embodiments are illustrative of the characteristics of the present invention so as to enable a person skilled in the art to understand the disclosed subject matter and implement the present invention accordingly. The embodiments, however, are not intended to restrict the scope of the present invention. Hence, all equivalent modifications and variations made in the foregoing embodiments without departing from the spirit and principle of the present invention should fall within the scope of the appended claims.

What is claimed is:
1. A spine fixation device, comprising:
a bone screw comprising:
a screw unit; and a fixation unit formed at a top end of the screw unit, the fixation unit having a top surface, the top surface being provided with an annular groove having a center defined by a center of the top surface, the top surface being centrally formed with a threaded hole, the top surface having an edge extending upward to form a first stop plate;

a fixation carrier comprising:

a hollow body having a wall formed with a pair of corresponding U-shaped openings;

a first extension unit extending downward from the hollow body, the first extension unit having a lateral portion extending outward to form a second stop plate, the second stop plate being rotatable between a first end and a second end of the first stop plate, the first extension unit being formed with an aperture which corresponds in position to the threaded hole and is in communication with the hollow body; and a second extension unit extending downward from the first extension unit so as to form a hollow annular projection to be rotatably coupled to the annular groove; and a first locking member to be locked in the threaded hole through the aperture, thereby conjugating the bone screw with the fixation carrier.

2. The spine fixation device of claim 1, wherein the bone screw is made of a metal or a metal alloy.

3. The spine fixation device of claim 1, wherein the first end and the second end are two corresponding ends of the first stop plate.

4. The spine fixation device of claim 1, wherein the fixation carrier is made of a metal or a metal alloy.

5. The spine fixation device of claim 1, wherein the first locking member is made of a metal or a metal alloy.

6. The spine fixation device of claim 1, further comprising a rod to be disposed in the pair of U-shaped openings.

7. The spine fixation device of claim 6, wherein the rod is made of a metal or a metal alloy.

8. The spine fixation device of claim 6, wherein the hollow body has an outer surface provided with a first thread structure.

9. The spine fixation device of claim 8, further comprising a second locking member internally provided with a second thread structure, the second thread structure being engageable with the first thread structure.

10. The spine fixation device of claim 9, wherein the second locking member is made of a metal or a metal alloy.

11. The spine fixation device of claim 1, wherein the hollow body has an inner surface provided with a third thread structure.

12. The spine fixation device of claim 11, further comprising a third locking member externally provided with a fourth thread structure, the fourth thread structure being engageable with the third thread structure.

13. The spine fixation device of claim 12, wherein the third locking member is made of a metal or a metal alloy.

* * * * *